(12) United States Patent
Momomoto et al.

(10) Patent No.: US 7,432,391 B2
(45) Date of Patent: Oct. 7, 2008

(54) PROCESS FOR THE PRODUCTION OF TERT-BUTYL N-(2-BROMOETHYL)CARBAMATE

(75) Inventors: Makoto Momomoto, Osaka (JP); Yoshiaki Suzuki, Osaka (JP); Minoru Yamagami, Osaka (JP); Keisuke Matsumoto, Osaka (JP); Yusuke Sakaguchi, Osaka (JP)

(73) Assignee: Daito Chemix Corporation, Osaka (JP)

( * ) Notice: Subject to any disclaimer, the term of this patent is extended or adjusted under 35 U.S.C. 154(b) by 0 days.

(21) Appl. No.: 11/795,025

(22) PCT Filed: May 24, 2005

(86) PCT No.: PCT/JP2005/009465

§ 371 (c)(1),
(2), (4) Date: Jul. 11, 2007

(87) PCT Pub. No.: WO2006/126255

PCT Pub. Date: Nov. 30, 2006

(65) Prior Publication Data

US 2008/0139839 A1    Jun. 12, 2008

(51) Int. Cl.
C07C 269/04    (2006.01)
C07C 269/08    (2006.01)
(52) U.S. Cl. ..................................... 560/161
(58) Field of Classification Search ........................ None
See application file for complete search history.

(56) References Cited

U.S. PATENT DOCUMENTS 6,184,233 B1 * 2/2001 Fujii et al. ................. 514/316

2004/0110744 A1    6/2004 Velker et al.

FOREIGN PATENT DOCUMENTS

| EP | 1 215 209 | 6/2002 |
| EP | 1 302 462 | 4/2003 |
| JP | 2002-201178 | 7/2002 |
| JP | 2002-322166 | 11/2002 |
| JP | 2002-332270 | 11/2002 |
| JP | 2004-529132 | 9/2004 |
| JP | 2005-206518 | 8/2005 |
| WO | 00/78763 | 12/2000 |

OTHER PUBLICATIONS

Vedejs et al, Journal of Organic Chemistry, Synthesis of Azocine Derivatives from Thioaldehyde Diels-Alder Adducts, 1988, 53, pp. 2226-2232.*
V. G. Beylin et al. "A Convenient Synthesis of t-butly N-(2-bromoethyl)carbamate", OPPI Briefs, vol. 19, No. 1, pp. 78-81 (1987).

* cited by examiner

Primary Examiner—Paul A Zucker
(74) Attorney, Agent, or Firm—Wenderoth, Lind & Ponack, L.L.P.

(57) ABSTRACT

The present invention is to provide a safe process for the production of tert-butyl N-(2-bromoethyl)carbamate where operation is simple, handling of the final product is easy, working efficiency is good and yield is high.

A process for the production of tert-butyl N-(2-bromoethyl) carbamate, characterized in that, 2-bromoethylamine or a salt thereof is made to react with an agent for introducing a tert-butoxy carbonyl group in a water-soluble solvent in the presence of sodium hydroxide and then water as a crystallizing solvent and seed crystals are added to the reaction solution whereby crystals of tert-butyl N-(2-bromoethyl)carbamate are separated out therefrom.

11 Claims, No Drawings

PROCESS FOR THE PRODUCTION OF TERT-BUTYL N-(2-BROMOETHYL)CARBAMATE

TECHNICAL FIELD OF THE INVENTION

The present invention relates to a novel process for the production of tert-butyl N-(2-bromoethyl)carbamate. Background Art tert-Butyl N-(2-bromoethyl)carbamate is a compound which is produced by the reaction of 2-bromoethylamine or a salt thereof with an agent for introduction of a tert-butoxy carbonyl (Boc) group (such as di-tert-butyl dicarbonate) (refer to the following chemical reaction formulae) and is a compound useful as a reaction intermediate for the synthesis of an inhibitor for an NO synthetase.

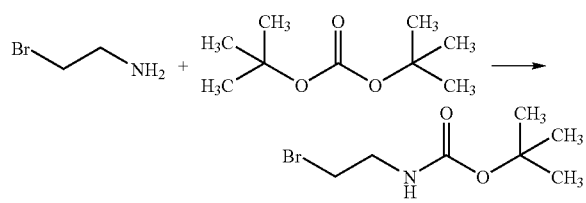

With regard to a process for the production of tert-butyl N-(2-bromoethyl)carbamate, the following ones, for example, have been known already.

In 6a) of Example 6 of Japanese Patent Laid-Open No. 2002/201,178, a process for the production of tert-butyl N-(2-bromoethyl)carbamate by the reaction of 2-bromoethylamine hydrobromide with di-tert-butyl dicarbonate in a mixture of acetonitrile and water in the presence of sodium hydroxide is disclosed. According to the process of Japanese Patent Laid-Open No. 2002/201,178, the reaction solution is extracted with ethyl acetate, washed, dried and concentrated whereupon tert-butyl N-(2-bromoethyl)carbamate is prepared as an oily substance.

In Example 11, column 28, of U.S. Pat. No. 6,329,523 B1, a process for the production of tert-butyl N-(2-bromoethyl) carbamate by the reaction of 2-bromoethylamine hydrobromide with di-tert-butyl dicarbonate in acetonitrile in the presence of triethylamine is disclosed. According to the process of U.S. Pat. No. 6,329,523 B1, the reaction solution is extracted with ether, dried and concentrated whereupon tert-butyl N-(2-bromoethyl)carbamate is prepared as an oily substance.

In A. of Example 7, column 33, of U.S. Pat. No. 5,741,912, a process for the production of tert-butyl N-(2-bromoethyl) carbamate by the reaction of 2-bromoethylamine hydrobromide with di-tert-butyl dicarbonate in a mixture of dioxane and water in the presence of sodium hydroxide is disclosed. According to the process of U.S. Pat. No. 5,741,912, the reaction solution is extracted with ether, dried and concentrated whereupon tert-butyl N-(2-bromoethyl)carbamate is prepared as an oily substance.

However, in all of those processes for the production of tert-butyl N-(2-bromoethyl)carbamate in the prior art, steps of extraction, washing and concentration are included as the steps for the preparation of tert-butyl N-(2-bromoethyl)carbamate from the reaction solution and not only the operation is complicated but also the yield is low. Moreover, tert-butyl N-(2-bromoethyl)carbamate prepared by those production processes of the prior art is an oily substance or a viscous liquid and does not become powder but is solidified into blocks upon cooling whereby its handling is difficult. Further, even under cooling, decomposition of the oily substance or the viscous liquid as such proceeds and stability is bad. Furthermore, the solvent used for the reaction and the solvent used for the extraction are entirely different from each other in those processes and, therefore, working efficiency is bad.

With regard to such a thing, there is a disclosure in V. G. Beylin and O. P. Goel (*Organic Preparations and Procedures International*, vol. 19, no. 1, pages 78 to 80 (1987)) concerning a process for the production of tert-butyl N-(2-bromoethyl)carbamate that 2-bromoethylamine hydrobromide is made to react with di-tert-butyl dicarbonate in a mixture of dichloromethane and water in the presence of sodium hydroxide, the reaction solution is extracted with dichloromethane followed by washing, drying and concentrating and then hexane as a crystallizing solvent is added thereto followed by stirring at −25° C. to −15° C. for one night whereupon crystals of tert-butyl N-(2-bromoethyl)carbamate are separated out.

However, in the method disclosed by V. G. Beylin and O. P. Goel, the yield is as very low as 71%. Moreover, since hexane is used as a crystallizing solvent, there is a risk of not only causing a damage of nerve system of persons conducting the work but also resulting in an electrostatic explosion whereby the method is not suitable for its industrialization. Furthermore, even in this method, the solvent used for the reaction and the solvent used for the crystallization are entirely different from each other and, therefore, its working efficiency is bad.

Accordingly, in all of the processes for the production of tert-butyl N-(2-bromoethyl)carbamate which have been known up to now, there is no satisfactory one due to their complicated operation, difficult handling of the final product, bad working efficiency, low yield or dangerous operation.

DISCLOSURE OF THE INVENTION

Problem that the Invention is to Solve

The present invention has been created in view of the actual state of the prior art as such and its object is to provide a safe process for the production of tert-butyl N-(2-bromoethyl) carbamate where operation is simple, handling of the final product is easy, working efficiency is good and yield is high.

Means for Solving the Problem

In order to achieve such an object, the present inventors have eagerly conducted a study for a method of efficient recovery of tert-butyl N-(2-bromoethyl)carbamate from the reaction solution and, as a result, they have found to recover tert-butyl N-(2-bromoethyl)carbamate by means of separation of crystals from the reaction solution using water as a crystallizing solvent whereupon the present invention has been accomplished.

Thus, the present invention is a process for the production of tert-butyl N-(2-bromoethyl)carbamate, characterized in that, 2-bromoethylamine or a salt thereof is made to react with an agent for introducing a tert-butoxy carbonyl (Boc) group in a water-soluble solvent in the presence of sodium hydroxide and then water as a crystallizing solvent and seed crystals are added to the reaction solution whereby crystals of tert-butyl N-(2-bromoethyl)carbamate are separated out therefrom.

In a preferred embodiment of the production process according to the present invention, the water-soluble solvent is selected from the group consisting of an alcohol (such as methanol, ethanol, propanol or butanol), a cyclic ether (such as tetrahydrofuran or 1,4-dioxane), a ketone (such as acetone), acetonitrile and a mixture thereof. The particularly preferred water-soluble solvent is methanol.

In a preferred embodiment of the present invention, the agent which introduces a tert-butoxy carbonyl group is selected from the group consisting of di-tert-butyl dicarbonate, Boc-ON, Boc-ONH$_2$, Boc-OCH(Cl)CCl$_3$, Boc-N$_3$, Boc-Cl, Boc-F and a mixture thereof. The particularly preferred agent for introducing a tert-butoxy carbonyl group is di-tert-butyl dicarbonate.

In a preferred embodiment of the production process according to the present invention, separation of crystals of tert-butyl N-(2-bromoethyl)carbamate is carried out at the temperature of −15 to 5° C.

In a preferred embodiment of the present invention, amount of water which is added to the reaction solution is from one-fold to three-fold of the weight of the agent for introduction of a tert-butoxy carbonyl group and, more preferably, it is three-fold.

In a preferred embodiment of the present invention, 2-bromoethylamine or a salt thereof is made to react with an agent for introduction of a tert-butoxy carbonyl group in a mixture of a water-soluble solvent and water in the presence of sodium hydroxide. The production process also comprises a step where the crystals which are separated out are recovered by filtration, washed with a mixture of a water-soluble solvent and water and dried.

Advantages of the Invention

In accordance with the production process of the present invention, recovery of tert-butyl N-(2-bromoethyl)carbamate from the reaction solution is not carried out by means of extraction, washing and concentration but is done by such a means that a crystallizing solvent and seed crystals are added to the reaction solution so that tert-butyl N-(2-bromoethyl)carbamate is separated out from the reaction solution as crystals and, accordingly, its operation is easy. In addition, since water is used as a crystallizing solvent, the operation is safe and the yield is high as well. In accordance with the production process of the present invention, the final product is prepared in a crystalline state and, therefore, its handling is easy. Moreover, in accordance with the production process of the present invention, the solvent used for the reaction and the solvent used for the crystallization are able to be made common with each other and, therefore, the working efficiency is good.

BEST MODE FOR CARRYING OUT THE INVENTION

The process for the production of tert-butyl N-(2-bromoethyl)carbamate in accordance with the present invention may be divided into two stages comprising a reaction stage where 2-bromoethylamine or a salt thereof is made to react with an agent for introduction of a tert-butoxy carbonyl group in a water-soluble solvent in the presence of sodium hydroxide whereby tert-butyl N-(2-bromoethyl)carbamate is produced and another stage for the recovery of the reaction product where water as a crystallizing solvent and seed crystals are added to the reaction solution whereby crystals of tert-butyl N-(2-bromoethyl)carbamate are separated out. As hereunder, the first-half reaction stage will be firstly illustrated and then the second-half stage for the recovery of the reaction product will be illustrated.

As to the salt of 2-bromoethylamine which is used as a starting material in the production process of the present invention, any salt may be used. For example, a hydrobromide may be used. As to an agent for the introduction of a tert-butoxy carbonyl group, any of known agents for the introduction of a tert-butoxy carbonyl group such as di-tert-butyl dicarbonate, Boc-ON, Boc-ONH$_2$, Boc-OCH(Cl)CCl$_3$, Boc-N$_3$, Boc-Cl, Boc-F and a mixture thereof may be used. In view of an easy industrial availability, it is preferred to use di-tert-butyl dicarbonate.

In the production process of the present invention, 2-bromoethylamine or a salt thereof which is a starting material is made to react with an agent for the introduction of a tert-butoxy carbonyl group in a water-soluble solvent in the presence of sodium hydroxide. With regard to the water-soluble solvent, an alcohol such as methanol, ethanol, propanol and butanol, a cyclic ether such as tetrahydrofuran and 1,4-dioxane, a ketone such as acetone, acetonitrile and a mixture thereof may be exemplified and, in view of the cost, it is preferred to use methanol. It is also possible to add water in addition to the water-soluble solvent. That is for washing sodium hydroxide thereinto.

In the production process of the present invention, preparation of the reaction solution may be carried out according to the following procedure for example. Thus, 2-bromoethylamine or a salt and a water-soluble solvent are charged in a flask and cooled down to −30 to 25° C. or, preferably, −10 to 0° C. and then an agent for introducing a tert-butoxy carbonyl group is added thereto; after that, an aqueous solution of sodium hydroxide is dropped thereinto at −30 to 30° C. or, preferably, −20 to 10° C. and then, if desired, water is added thereto. In the production process of the present invention, it is desirable in view of the reaction efficiency to conduct the reaction at −30 to 30° C. or, preferably, −10 to 10° C. for 5 to 36 hours.

After finishing the reaction, the reaction product is recovered from the reaction solution. In the production process of the present invention, recovery of the reaction product is carried out by such a manner that water as a crystallizing solvent and seed crystals are added to the reaction solution whereby crystals of tert-butyl N-(2-bromoethyl)carbamate are separated out therefrom. Although there is no particular limitation for the amount of water to be added to the reaction solution, it is preferred to be from one-fold to three-fold of the weight of the agent for introducing a tert-butoxy carbonyl group in view of the separation efficiency. When the amount of water added to the reaction solution is less than one-fold of the weight of the agent for introducing a tert-butoxy carbonyl group, loss of the filtrate becomes too much and that is not preferred. The loss of the filtrate is 10 to 12%, 3 to 4% and 1 to 2% when the amount of water added to the reaction solution is one-fold, two-fold and three-fold, respectively, of the weight of the agent for introducing a tert-butoxy carbonyl group. Even when water in an amount of more than three-fold of the weight of the agent for introducing a tert-butoxy carbonyl group is added to the reaction solution, the loss of the filtrate does not become smaller and there is no difference in the effect. Accordingly, the particularly preferred amount of water is three-fold of the weight of the agent for introducing a tert-butoxy carbonyl group. Although the water may be added to the reaction solution at a time, the aimed product and the solvent are separated into two layers if water is added at a time whereby there is a risk that crystals become too big and, therefore, it is desirable that water is added by dividing into plural times. For example, when water in an amount of three-fold of the weight of the agent for introducing a tert-butoxy carbonyl group is added to the reaction solution, water in an amount of one-fold is firstly added thereto so that a part of crystals are separated out and then water in an amount of two-fold which is the residual amount is added so that all of the crystals are separated out therefrom.

In the production process of the present invention, it is preferred that separation of crystals of tert-butyl N-(2-bromoethyl)carbamate is carried out at −15 to 5° C. and, more preferably, at −5 to 0° C. Time for the separation is preferred to be about 1 to 48 hour(s).

Crystals of the separated tert-butyl N-(2-bromoethyl)carbamate are recovered, for example, by filtration and then washed with a mixture of a water-soluble solvent used for the reaction and water followed by drying.

According to the steps as mentioned above, tert-butyl N-(2-bromoethyl)carbamate is able to be produced in a crystalline state which is easy for handling, in a simple operation, in a good working efficiency, in a high yield and in a safe manner.

EXAMPLES

The process for production according to the present invention will now be illustrated in a more specific manner by way of Examples. Incidentally, descriptions of the Examples are given here purely for the understanding of the invention and the present invention is not limited by them at all.

Example 1

An Example where the Amount of Water to be Added to the Reaction Solution was Made 3-fold of the Weight of the Agent for Introducing a tert-butoxy carbonyl Group 2-Bromoethylamine hydrobromide (575 g) and 765 g of methanol were charged in a flask and cooled down to −5° C. and 510 g of di-tert-butyl dicarbonate was added thereto. After that, 387 g of a 29% aqueous solution of sodium hydroxide was dropped thereinto, then 102 g of water was added thereto and the mixture was made to react at −10 to 10° C. for 5 hours. Then 510 g of water was added, the mixture was cooled down to 3° C. or lower and seed crystals were poured thereinto. Further, 1,020 g of water was dropped thereinto at 3° C. or lower, the mixture was kept at 3° C. or lower for 1 hour and the crystals separated out therefrom were filtered. The resulting crystals were washed with methanol/water and dried to give 487 g of crystals of tert-butyl N-(2-bromoethyl)carbamate (yield: 93%; NMR purity: 100%).

Example 2

An Example Where the Amount of Water to be Added to the Reaction Solution was Made 2-fold of the Weight of the Agent for Introducing a tert-butoxy carbonyl Group 2-Bromoethylamine hydrobromide (575 g) and 765 g of methanol were charged in a flask and cooled down to −5° C. and 510 g of di-tert-butyl dicarbonate was added thereto. After that, 387 g of a 29% aqueous solution of sodium hydroxide was dropped thereinto, then 102 g of water was added thereto and the mixture was made to react at −10 to 10° C. for 5 hours. Then 510 g of water was added, the mixture was cooled down to 3° C. or lower and seed crystals were poured thereinto. Further, 510 g of water was dropped thereinto at 3° C. or lower, the mixture was kept at 3° C. or lower for 1 hour and the crystals separated out therefrom were filtered. The resulting crystals were washed with methanol/water and dried to give 477 g of crystals of tert-butyl N-(2-bromoethyl)carbamate (yield: 91%; NMR purity: 100%).

Example 3

An Example Where the Amount of Water to be Added to the Reaction Solution was Made 1-fold of the Weight of the Agent for Introducing a tert-butoxy carbonyl Group 2-Bromoethylamine hydrobromide (575 g) and 765 g of methanol were charged in a flask and cooled down to −5° C. and 510 g of di-tert-butyl dicarbonate was added thereto. After that, 387 g of a 29% aqueous solution of sodium hydroxide was dropped thereinto, then 102 g of water was added thereto and the mixture was made to react at −10 to 10° C. for 5 hours. Then 510 g of water was added, the mixture was cooled down to 3° C. or lower and seed crystals were poured thereinto. Further, the mixture was kept at 3° C. or lower for 1 hour and the crystals separated out therefrom were filtered. The resulting crystals were washed with methanol/water and dried to give 435 g of crystals of tert-butyl N-(2-bromoethyl)carbamate (yield: 83%; NMR purity: 100%).

Comparative Example 1

Follow-Up Test of 6a of Example 6 in Japanese Patent Laid-Open No. 2002/201,178

2-Bromoethylamine hydrobromide (5 g) was dissolved in 30.5 ml of water and 30.5 ml of acetonitrile, 30.5 ml of a 2N aqueous solution of sodium hydroxide and 5.9 g of di-tert-butyl dicarbonate were added thereto and the mixture was stirred for 15 hours. The reaction solution was concentrated, water was added to the residual solution, the mixture was extracted with ethyl acetate and the extract was washed with a diluted aqueous solution of potassium hydrogensulfate and a saturated aqueous saline solution in this order and dried over anhydrous sodium sulfate. The extract was concentrated to give 5.0 g (yield: 82%) of tert-butyl N-(2-bromoethyl)carbamate as an oily substance (incidentally, the yield calculated on the basis of purity by NMR was 65%).

Comparative Example 2

Follow-Up Test of Example 11 in U.S. Pat. No. 6,329,523 B1

2-Bromoethylamine hydrobromide (5 g) was dissolved in 87.4 ml of acetonitrile and 3.6 ml of triethylamine and 5.0 g of di-tert-butyl dicarbonate were added thereto. The reaction solution was stirred for 12 hours at 20 to 25° C. in a nitrogen stream, then 70 ml of a saturated aqueous solution of sodium bicarbonate was added thereto and the mixture was extracted with 100 ml of ether. The ether layer was separated, dried over Glauber's salt and concentrated using an evaporator to give 4.8 g (apparent yield: 94%) of tert-butyl N-(2-bromoethyl) carbamate as an oily substance (incidentally, the yield calculated on the basis of purity by NMR was 82%).

Comparative Example 3

Follow-Up Test of A of Example 7 in U.S. Pat. No. 5,741,912

2-Bromoethylamine hydrobromide (5 g) was added to a dispersion of 2.6 g of sodium carbonate in 49 ml of dioxane-water (2:1) and the mixture was stirred at 0° C. for 15 minutes. After that, 5.4 g of di-tert-butyl dicarbonate was added thereto and the mixture was stirred at 0° C. for 1 hour and then made to react at 20 to 25° C. for 12 hours. After evaporating the solvent using an evaporator, 65 ml of water was added to the residue and the mixture was extracted with 80 ml of ether. The ether layer was washed with water, dried over Glauber's salt and concentrated by an evaporator again to give 4.8 g (apparent yield: 94%) of tert-butyl N-(2-bromoethyl)carbamate as an oily substance (incidentally, the yield calculated on the basis of purity by NMR was 68%).

It is apparent by comparison of Examples 1 to 3 with Comparative Examples 1 to 3 that tert-butyl N-(2-bromoethyl)carbamate was recovered by extraction from the reaction solvent, washing and concentration in the method of the Comparative Examples whereby its operation is complex and, in addition, the yield is low as well. Further, since the resulting tert-butyl N-(2-bromoethyl)carbamate is an oily substance, its handling is difficult. Furthermore, in the method of the Comparative Examples, the solvent used for the reaction and the solvent used for the extraction are entirely different from each other and, therefore, the working efficiency is very bad.

On the contrary, in the method of the Examples according to the present invention, tert-butyl N-(2-bromoethyl)carbamate is recovered by means of separation of crystals from the reaction solution and, therefore, the operation is easy and, in addition, the yield is high as well. Further, the resulting tert-butyl N-(2-bromoethyl)carbamate is in a crystalline state and, therefore, its handling is easy. Furthermore, in the method of the Examples according to the present invention, the solvent (methanol/water) used for the reaction and the solvent (water) used for the crystallization are partially common with each other and, therefore, the working efficiency is good. Moreover, in the method of the Examples according to the present invention, the solvent used for the crystallization is water and, therefore, safety is very high. Accordingly, in accordance with the production process of the present invention, tert-butyl N-(2-bromoethyl)carbamate which is useful as a reaction intermediate for the synthesis of an NO synthetase inhibitor is now able to be efficiently produced in an industrial scale.

The invention claimed is:

1. A process for the production of tert-butyl N-(2-bromoethyl)carbamate, wherein 2-bromoethylamine or a salt thereof is made to react with an agent for introducing a tert-butoxy carbonyl group in a water-soluble solvent in the presence of sodium hydroxide and then water as a crystallizing solvent and seed crystals are added to the reaction solution whereby crystals of tert-butyl N-(2-bromoethyl)carbamate are separated out therefrom.

2. The process for the production of tert-butyl N-(2-bromoethyl)carbamate according to claim 1, wherein the water-soluble solvent is selected from the group consisting of an alcohol, a cyclic ether, a ketone, acetonitrile and a mixture thereof.

3. The process for the production of tert-butyl N-(2-bromoethyl)carbamate according to claim 2, wherein the water-soluble solvent is selected from the group consisting of methanol, ethanol, propanol, butanol, tetrahydrofuran, 1,4-dioxane, acetone, acetonitrile and a mixture thereof.

4. The process for the production of tert-butyl N-(2-bromoethyl)carbamate according to claim 3, wherein the water-soluble solvent is methanol.

5. The process for the production of tert-butyl N-(2-bromoethyl)carbamate according to claim 1, wherein the agent which introduces a tert-butoxy carbonyl group is selected from the group consisting of di-tert-butyl dicarbonate, Boc-ON, Boc-ONH$_2$, Boc-OCH(Cl)CCl$_3$, Boc-N$_3$, Boc-Cl, Boc-F and a mixture thereof.

6. The process for the production of tert-butyl N-(2-bromoethyl)carbamate according to claim 5, wherein the agent for introducing a tert-butoxy carbonyl group is di-tert-butyl dicarbonate.

7. The process for the production of tert-butyl N-(2-bromoethyl)carbamate according to claim 1, wherein separation of crystals of tert-butyl N-(2-bromoethyl)carbamate is carried out at the temperature of −15 to 5° C.

8. The process for the production of tert-butyl N-(2-bromoethyl)carbamate according to claim 1, wherein amount of water which is added to the reaction solution is from one-fold to three-fold of the weight of the agent for introduction of a tert-butoxy carbonyl group.

9. The process for the production of tert-butyl N-(2-bromoethyl)carbamate according to claim 8, wherein amount of water which is added to the reaction solution is three-fold of the weight of the agent for introduction of a tert-butoxy carbonyl group.

10. The process for the production of tert-butyl N-(2-bromoethyl)carbamate according to claim 1, wherein 2-bromoethylamine or a salt thereof is made to react with an agent for introduction of a tert-butoxy carbonyl group in a mixture of a water-soluble solvent and water in the presence of sodium hydroxide.

11. The process for the production of tert-butyl N-(2-bromoethyl)carbamate according to claim 1, wherein the crystals which are separated out are recovered by filtration, washed with a mixture of a water-soluble solvent and water and dried.

* * * * *